United States Patent
Takakuwa et al.

(10) Patent No.: US 11,155,507 B2
(45) Date of Patent: Oct. 26, 2021

(54) METHOD FOR PRODUCING REACTION GAS CONTAINING (E)-1,2-DIFLUOROETHYLENE

(71) Applicant: DAIKIN INDUSTRIES, LTD., Osaka (JP)

(72) Inventors: Tatsuya Takakuwa, Osaka (JP); Osamu Yamamoto, Osaka (JP); Katsuki Fujiwara, Osaka (JP); Kei Kuramoto, Osaka (JP); Yuuta Hasumoto, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 0 days.

(21) Appl. No.: 17/130,421

(22) Filed: Dec. 22, 2020

(65) Prior Publication Data

US 2021/0107850 A1    Apr. 15, 2021

Related U.S. Application Data

(63) Continuation of application No. PCT/JP2020/022443, filed on Jun. 5, 2020.

(30) Foreign Application Priority Data

Jun. 7, 2019    (JP) .............................. JP2019-106863

(51) Int. Cl.
| | | |
|---|---|---|
| *C07C 17/269* | (2006.01) | |
| *C07C 17/278* | (2006.01) | |
| *C07C 21/18* | (2006.01) | |
| *C09K 5/04* | (2006.01) | |

(52) U.S. Cl.
CPC .......... *C07C 17/278* (2013.01); *C07C 17/269* (2013.01); *C09K 5/045* (2013.01); *C09K 2205/126* (2013.01)

(58) Field of Classification Search
CPC .... C07C 17/275; C07C 17/269; C07C 17/278
See application file for complete search history.

(56) References Cited

U.S. PATENT DOCUMENTS

| | | |
|---|---|---|
| 2015/0322317 A1 | 11/2015 | Collier et al. |
| 2017/0058172 A1 | 3/2017 | Fukushima et al. |
| 2017/0058173 A1 | 3/2017 | Fukushima |
| 2017/0058174 A1 | 3/2017 | Fukushima et al. |

FOREIGN PATENT DOCUMENTS

| | | | |
|---|---|---|---|
| JP | 2012-237472 | 12/2012 | |
| JP | 2013-241348 | 12/2013 | |
| WO | WO-9601241 A1 * | 1/1996 | ........... C07C 17/206 |
| WO | 2015/186557 | 12/2015 | |
| WO | 2015/186670 | 12/2015 | |
| WO | 2015/186671 | 12/2015 | |

OTHER PUBLICATIONS

Patent No. JP2013241348A, English translation, Dec. 2013, pp. 1-11 (Year: 2013).*
International publication No. WO1996001241A1, Jan. 1996, pp. 1-7 (Year: 1996).*
McCoy, H. E. et al. "Corrosion of Several Metals in Supercritical Steam at 538° C." Published May 1977 (Year: 1977).*
International Search Report dated Sep. 1, 2020 in International (PCT) Application No. PCT/JP2020/022443.

* cited by examiner

*Primary Examiner* — Medhanit W Bahta
(74) *Attorney, Agent, or Firm* — Wenderoth, Lind & Ponack, L.L.P.

(57) ABSTRACT

The present disclosure provides a method for producing a reaction gas containing R-1132(E) with selectivity higher than that of known methods. Specifically, the present disclosure provides a method for producing a reaction gas containing (E)-1,2-difluoroethylene (R-1132(E)), (1) the method comprising a step of subjecting a starting material gas containing one or more fluoromethanes selected from the group consisting of chlorodifluoromethane (R-22), difluoromethane (R-32), and fluoromethane (R-41) to a reaction that involves thermal decomposition to obtain the reaction gas, and (2) the starting material gas having a water vapor content of 1 volume % or less.

3 Claims, No Drawings

METHOD FOR PRODUCING REACTION GAS CONTAINING (E)-1,2-DIFLUOROETHYLENE

TECHNICAL FIELD

The present disclosure relates to a method for producing a reaction gas containing (E)-1,2-difluoroethylene.

BACKGROUND ART (E)-1,2-Difluoroethylene (also referred to below as "R-1132(E)"), which has a low global warming potential (GWP), is attracting attention as an alternative refrigerant for difluoromethane (R-32) or 1,1,1,2,2-pentafluoroethane (R-125), which are greenhouse gases.

Patent Literature (PTL) 1 discloses a method for producing 1,2-difluoroethylene by a synthesis reaction accompanying thermal decomposition from a compound represented by formula (1): $CH_2FX$ (1) (wherein X is a halogen atom).

CITATION LIST

Patent Literature

PTL 1: JP2013-241348A

SUMMARY OF INVENTION

Technical Problem

An object of the present disclosure is to provide a method for producing a reaction gas containing R-1132(E) with higher selectivity than that of known methods.

Solution to Problem

For example, the present disclosure includes the subject matter described in the following items.

Item 1. A method for producing a reaction gas containing (E)-1,2-difluoroethylene (R-1132(E)),
(1) the method comprising a step of subjecting a starting material gas containing one or more fluoromethanes selected from the group consisting of chlorodifluoromethane (R-22), difluoromethane (R-32), and fluoromethane (R-41) to a reaction that involves thermal decomposition to obtain the reaction gas, and
(2) the starting material gas having a water vapor content of 1 volume % or less.

Item 2. A method for producing a reaction gas containing (E)-1,2-difluoroethylene (R-1132(E)),
(1) the method comprising a step of subjecting a starting material gas containing one or more fluoromethanes selected from the group consisting of chlorodifluoromethane (R-22), chlorofluoromethane (R-31), difluoromethane (R-32), and fluoromethane (R-41) to a reaction that involves thermal decomposition to obtain the reaction gas, and
(2) the reaction being performed by using a metal reactor with an iron content of 10 mass % or less.

Item 3. A method for producing a reaction gas containing (E)-1,2-difluoroethylene (R-1132(E)),
(1) the method comprising a step of subjecting a starting material gas containing one or more fluoromethanes selected from the group consisting of chlorodifluoromethane (R-22), chlorofluoromethane (R-31), difluoromethane (R-32), and fluoromethane (R-41) to a reaction that involves thermal decomposition to obtain the reaction gas, and
(2) the starting material gas containing one or more inert gases selected from the group consisting of nitrogen, argon, hydrofluorocarbons, and carbon dioxide in an amount of 10 to 90 volume %.

Item 4. A method for producing a reaction gas containing (E)-1,2-difluoroethylene (R-1132(E)),
(1) the method comprising a step of subjecting a starting material gas containing one or more fluoromethanes selected from the group consisting of chlorodifluoromethane (R-22), chlorofluoromethane (R-31), difluoromethane (R-32), and fluoromethane (R-41) to a reaction that involves thermal decomposition to obtain the reaction gas, and
(2) the starting material gas containing the fluoromethanes in an amount of 90 to 100 volume %.

Item 5. The production method according to any one of Items 1 to 4, wherein the starting material gas contains R-32.

Item 6. The production method according to any one of Items 1 to 5, wherein the reaction is performed at a temperature of 750 to 1050° C.

Item 7. The production method according to any one of Items 1 to 6, wherein the reaction is performed at a pressure of 0 to 0.6 MPaG.

Item 8. A composition comprising (E)-1,2-difluoroethylene (R-1132(E)) and one or more compounds selected from the group consisting of 3,3,3-trifluoropropyne (TFP), propyne, and 1,1,1,2-tetrafluoroethane (R-134a).

Item 9. The composition according to Item 8, wherein the content of TFP is 1 mass % or less based on the total amount of the composition.

Advantageous Effects of Invention

The method for producing a reaction gas containing R-1132(E) according to the present disclosure is capable of producing R-1132(E) with higher selectivity (selectivity in reaction gas) than known methods.

DESCRIPTION OF EMBODIMENTS

In the present specification, the term "conversion" refers to the ratio (mol %) of the total molar concentration of compounds other than fluoromethanes contained in the gas (=reaction gas) flowing out of the reactor outlet to the molar concentration of fluoromethanes supplied to the reactor.

In the present specification, the term "selectivity" refers to the ratio (mol %) of the molar concentration of the target compound (R-1132(E)) contained in the gas (=reaction gas) flowing out of the reactor outlet to the total molar concentration of compounds other than fluoromethanes contained in the gas.

In the present specification, a numerical range indicated by "... to ..." means a range including the numerical values before and after "to" as the lower limit and the upper limit.

The method for producing a reaction gas containing (E)-1,2-difluoroethylene (R-1132(E)) according to the present disclosure comprises a step of subjecting a starting material gas containing one or more fluoromethanes selected from the group consisting of chlorodifluoromethane (R-22), chlorofluoromethane (R-31), difluoromethane (R-32), and fluoromethane (R-41) to a reaction that involves thermal decomposition (synthesis reaction accompanying thermal decomposition of the fluoromethanes), thus obtaining the reaction gas containing R-1132(E). More specifically, the method can be roughly divided into the following embodiments 1 to 4.

Embodiment 1

A method for producing a reaction gas containing (E)-1,2-difluoroethylene (R-1132(E)),
(1) the method comprising a step of subjecting a starting material gas containing one or more fluoromethanes selected from the group consisting of chlorodifluoromethane (R-22), difluoromethane (R-32), and fluoromethane (R-41) to a reaction that involves thermal decomposition to obtain the reaction gas, and
(2) the starting material gas having a water vapor content of 1 volume % or less.

Embodiment 2

A method for producing a reaction gas containing (E)-1,2-difluoroethylene (R-1132(E)),
(1) the method comprising a step of subjecting a starting material gas containing one or more fluoromethanes selected from the group consisting of chlorodifluoromethane (R-22), chlorofluoromethane (R-31), difluoromethane (R-32), and fluoromethane (R-41) to a reaction that involves thermal decomposition to obtain the reaction gas, and
(2) the reaction being performed by using a metal reactor with an iron content of 10 mass % or less.

Embodiment 3

A method for producing a reaction gas containing (E)-1,2-difluoroethylene (R-1132(E)),
(1) the method comprising a step of subjecting a starting material gas containing one or more fluoromethanes selected from the group consisting of chlorodifluoromethane (R-22), chlorofluoromethane (R-31), difluoromethane (R-32), and fluoromethane (R-41) to a reaction that involves thermal decomposition to obtain the reaction gas, and
(2) the starting material gas containing one or more inert gases selected from the group consisting of nitrogen, argon, hydrofluorocarbons, and carbon dioxide in the content of 10 to 90 volume %.

Embodiment 4

A method for producing a reaction gas containing (E)-1,2-difluoroethylene (R-1132(E)),
(1) the method comprising a step of subjecting a starting material gas containing one or more fluoromethanes selected from the group consisting of chlorodifluoromethane (R-22), chlorofluoromethane (R-31), difluoromethane (R-32), and fluoromethane (R-41) to a reaction that involves thermal decomposition to obtain the reaction gas, and
(2) the starting material gas containing the fluoromethanes in the content of 90 to 100 volume %.

The methods for producing a reaction gas containing R-1132(E) according to the present disclosure having the above characteristics are capable of producing a reaction gas containing R-1132(E) with higher selectivity (selectivity in reaction gas) than that of known methods.

1. Method for Producing Reaction Gas Containing R-1132(E)

Below, embodiments 1 to 4 mentioned above are described individually.

Embodiment 1

Embodiment 1 relates to a method for producing a reaction gas containing R-1132(E),
(1) the method comprising a step of subjecting a starting material gas containing one or more fluoromethanes selected from the group consisting of chlorodifluoromethane (R-22), difluoromethane (R-32), and fluoromethane (R-41) to a reaction that involves thermal decomposition to obtain the reaction gas, and
(2) the starting material gas having a water vapor content of 1 volume % or less.

The starting material gas contains one or more fluoromethanes selected from the group consisting of chlorodifluoromethane (R-22), difluoromethane (R-32), and fluoromethane (R-41), which are capable of synthesizing a reaction gas containing R-1132(E), which is the target compound, by a reaction that involves thermal decomposition (also simply referred to below as "the reaction"). Among these fluoromethanes, R-32 is preferable from the viewpoint of suppressing the formation of by-products.

In embodiment 1, the starting material gas has a water vapor content of 1 volume % or less. Due to this, the selectivity of R-1132(E) in the reaction gas is improved. It is sufficient if the water vapor content in the starting material gas is 1 volume % or less; however, in the best embodiment, it is preferable that the starting material gas contains no water vapor. That is, the starting material gas may consist essentially of the fluoromethanes (one or more members selected from the group consisting of R-22, R-32, and R-41). In embodiment 1, it is preferable that the starting material gas also has a low water vapor content from the viewpoint of the formation of by-products. The upper limit of the water vapor content in the starting material gas is preferably 1 volume %, more preferably 0.5 volume %, and particularly preferably 0.1 volume %. Further, in embodiment 1, the lower limit of the water vapor content in the starting material gas is preferably 0 volume ppm, more preferably 0.1 volume ppm, and particularly preferably 1 volume ppm. In embodiment 1, when the water vapor content in the starting material gas is 0 volume ppm, performing dehydration treatment is difficult, and the process control is complicated; however, this is not problematic.

In embodiment 1, the starting material gas has a water vapor content of 1 volume % or less. Due to this, although the starting material conversion is lowered, both the selectivity of R-1132(E) in the reaction gas and yield of R-1132(E) can be improved more than in known methods. In particular, the selectivity of R-1132(E) in the reaction gas can be increased to 15 mol % or more, which is a great advantage over known techniques.

In embodiment 1, it is preferable that the starting material gas contains R-32, and has a water vapor content of 1 volume % or less. In embodiment 1, it is more preferable that the starting material gas contains R-32, and has a water vapor content of 0 volume % or more and 0.5 volume or less. In embodiment 1, it is particularly preferable that the starting material gas contains R-32, and has a water vapor content of 0 volume % or more and 0.1 volume % or less.

In embodiment 1, the fluoromethanes alone may be directly supplied to a reactor as the starting material gas; or the fluoromethanes may be supplied after being diluted with an inert gas, such as nitrogen, argon, or carbon dioxide. It is also possible to supply the starting material gas after the starting material gas is preheated to an arbitrary temperature, if necessary.

The temperature (reaction temperature) at which the starting material gas is subjected to the reaction is preferably 750 to 1050° C., more preferably 800 to 950° C., and still more preferably 850 to 900° C. When the reaction temperature is set within this range, both the conversion of fluoromethanes and the selectivity of R-1132(E) can be improved. in particular, when the reaction temperature is set to 850° C. or higher, trifluoroethylene (R-1123) is easily contained in the reaction gas in addition to R-1132(E). This is advantageous because R-1132(E) and R-1123, which are promising refrigerants, can be simultaneously produced. To achieve such simultaneous production, the reaction temperature is preferably set to 850 to 1050° C., more preferably 850 to 950° C., and particularly preferably 850 to 900° C.

The heating method used when subjecting the starting material gas to the reaction may be a known method. Examples include a method of heating a reactor (reaction container) in an electric furnace, a method of heating a reactor with an electric heater or a jacket through which a heat medium is circulated, a method of heating a reactor in a microwave oven, and a method in which the inert gas as a diluent gas is heated and then mixed with fluoromethanes. If necessary, the starting material gas may be supplied after the starting material gas is preheated to an arbitrary temperature.

The pressure (reaction pressure) at which the starting material gas is supplied to the reaction is preferably 0 to 0.6 MPaG, and more preferably 0 to 0.3 MPaG. By setting the pressure within this range, both the conversion of fluoromethanes and the selectivity of R-1132(E) can be improved. The lower limit of the pressure can be set to, for example, 0.01 MPaG or 0.1 MPaG.

The time (residence time) for subjecting the starting material gas to the reaction is in accordance with the type of fluoromethanes, reaction temperature, reaction pressure, and the like; and cannot be unconditionally determined. However, it is preferably 0.2 to 3 seconds, and more preferably 0.5 to 1 second. When the residence time is set to a value equal to or more than the lower limit of the above range, the thermal decomposition of fluoromethanes is promoted, and R-1132(E) is obtained efficiently. When the residence time is set to a value equal to or less than the upper limit of the above range, side reactions are suppressed, and thermal decomposition of fluoromethanes is promoted, improving the productivity. When the reaction temperature is set to 850 to 1050° C. for the purpose of simultaneously producing (co-producing) R-1132(E) and R-1123, it is preferable to set the residence time to 0.1 to 0.5 seconds.

The form of the reactor in which the starting material gas is subjected to the reaction is not limited, and known reactors capable of withstanding the reaction temperature and reaction pressure stated above are widely usable. For example, a tubular flow reactor packed with a catalyst may be used. Examples of the catalyst include metal oxide catalysts, such as $Al_2O_3$ and $CoO_2$; metal catalysts, such as Fe, Zn, and Co; and catalysts in which metal particles are supported on oxide or carbon carriers, such as Pd/C and Pd/TiO$_2$. When the reaction is performed in the absence of a catalyst, the reactor may be, for example, a hollow adiabatic reactor, or an adiabatic reactor packed with a porous or non-porous metal or medium that improves the mixing state of the starting material gas. Also usable is a multitubular reactor or the like in which a heat medium is used to cool the reactor and/or to homogenize the temperature distribution within the reactor.

When a hollow reactor is used, in a method wherein a reactor with a smaller inner diameter is used to improve heat transfer efficiency, it is preferable, for example, that the relationship between the flow rate of the starting material gas and the inner diameter of the reactor be adjusted so that a high linear velocity and a large heat transfer area are obtained.

Specifically, the reactor is preferably formed of a material that is resistant to the corrosive action, such as Hastelloy, Inconel, Monel, Incoloy, and stainless steel materials (e.g., SUS316). Although the details are described in embodiment 2, when a metal reactor with an iron content of 10 mass % or less, such as a reactor of Hastelloy or Inconel, is used from among the reactors above, the occurrence of caulking on the reactor inner wall can also be suppressed in a manner more excellent than in known methods.

The reaction gas containing R-1132(E) obtained in embodiment 1 may be appropriately subjected to a purification step to extract high-purity R-1132(E). The purification method may be a known purification method, such as distillation.

The reaction gas containing R-1132(E) obtained in embodiment 1 more preferably further contains R-1123 and R-32. That is, in the present disclosure, the reaction gas obtained in embodiment 1 more preferably contains R-1132(E), R-1123, and R-32.

Embodiment 2

Embodiment 2 relates to a method for producing a reaction gas containing R-1132(E),
(1) the method comprising a step of subjecting a starting material gas containing one or more fluoromethanes selected from the group consisting of chlorodifluoromethane (R-22), chlorofluoromethane (R-31), difluoromethane (R-32), and fluoromethane (R-41) to a reaction that involves thermal decomposition to obtain the reaction gas, and
(2) the reaction being performed by using a metal reactor with an iron content of 10 mass % or less.

The starting material gas contains one or more fluoromethanes selected from the group consisting of chlorodifluoromethane (R-22), chlorofluoromethane (R-31), difluoromethane (R-32), and fluoromethane (R-41), which are capable of synthesizing a reaction gas containing R-1132(E), which is the target compound, by a reaction that involves thermal decomposition. Among these fluoromethanes, R-32 is preferable from the viewpoint of suppressing the formation of by-products.

In embodiment 2, fluoromethanes alone may be directly supplied to a reactor as the starting material gas, or the fluoromethanes may be supplied after being diluted with an inert gas, such as nitrogen, argon, or carbon dioxide. It is also possible to supply the starting material gas after the starting material gas is preheated to an arbitrary temperature, if necessary.

In embodiment 2, the reaction above is performed by using a metal reactor with an iron content of 10 mass % or less. Examples of the metal reactor include those of Hastelloy, Incoloy, Inconel, and Monel. In embodiment 2, it is particularly preferable to use a reactor of Inconel as the metal reactor with an iron content of 10 mass % or less. In embodiment 2, the reaction is performed by using a metal reactor with an iron content of 10 mass % or less. Due to this, the occurrence of caulking on the reactor inner wall can be suppressed in a manner more excellent than in known methods. Additionally, the generation of $CO_2$ due to the reaction between the reactor inner wall and the starting material gas can be suppressed more than in known methods.

For example, the reaction behavior in regards to the generation of $CO_2$ is presumed to be such that fluoromethanes are thermally decomposed in a region in which the reaction temperature is relatively high to generate fluorine radicals, the fluorine radicals are replaced with oxygen atoms in the vicinity of iron atoms contained in the metal reactor to generate oxygen radicals, and the oxygen radicals undergo reaction at the caulked reactor inner wall to generate $CO_2$. The use of a metal reactor with an iron content of 10 mass % or less as in embodiment 2 can suppress the generation of $CO_2$ based on the behavior described above as an example.

The form of the reactor in which the starting material gas is subjected to the reaction is not limited as long as the iron content is within the above range, and known reactors capable of withstanding the reaction temperature and reaction pressure mentioned later are widely usable. For example, a tubular flow reactor packed with a catalyst may be used. Examples of the catalyst include metal oxide catalysts, such as $Al_2O_3$ and $CoO_2$; metal catalysts, such as Fe, Zn, and Co; and catalysts in which metal particles are supported on oxide or carbon carriers, such as Pd/C and $Pd/TiO_2$. When the reaction is performed in the absence of a catalyst, the reactor may be, for example, a hollow adiabatic reactor, or an adiabatic reactor packed with a porous or non-porous metal or medium that improves the mixing state of the starting material gas. Also usable is a multitubular reactor or the like in which a heat medium is used to cool the reactor and/or to homogenize the temperature distribution within the reactor.

When a hollow reactor is used, in a method wherein a reactor with a smaller inner diameter is used to improve heat transfer efficiency, it is preferable, for example, that the relationship between the flow rate of the starting material gas and the inner diameter of the reactor be adjusted so that a high linear velocity and a large heat transfer area are obtained.

The temperature (reaction temperature) at which the starting material gas is subjected to the reaction is preferably 750 to 1050° C., more preferably 800 to 950° C., and still more preferably 850 to 900° C. When the reaction temperature is set within this range, both the conversion of fluoromethanes and the selectivity of R-1132(E) can be improved. In particular, when the reaction temperature is set to 850° C. or higher, trifluoroethylene (R-1123) is easily contained in the reaction gas in addition to R-1132(E). This is advantageous because R-1132(E) and R-1123, which are promising refrigerants, can be simultaneously produced (co-produced). To achieve such simultaneous production (co-production), the reaction temperature is preferably set to 850 to 1050° C., more preferably 850 to 950° C., and particularly preferably 850 to 900° C.

The heating method used when subjecting the starting material gas to the reaction may be a known method. Examples include a method of heating a reactor (reaction container) in an electric furnace, a method of heating a reactor with an electric heater or a jacket through which a heat medium is circulated, a method of heating a reactor in a microwave oven, and a method in which the inert gas as a diluent gas is heated and then mixed with fluoromethanes.

If necessary, the starting material gas may be supplied after the starting material gas is preheated to an arbitrary temperature.

The pressure (reaction pressure) at which the starting material gas is supplied to the reaction is preferably 0 to 0.6 MPaG (gauge pressure), and more preferably 0 to 0.3 MPaG. By setting the pressure within this range, both the conversion of fluoromethanes and the selectivity of R-1132 (E) can be improved. The lower limit of the pressure can be set to, for example, 0.01 MPaG or 0.1 MPaG.

The time (residence time) for subjecting the starting material gas to the reaction is in accordance with the type of fluoromethanes, reaction temperature, reaction pressure, and the like; and cannot be unconditionally determined. However, it is preferably 0.2 to 3 seconds, and more preferably 0.5 to 1 second. When the residence time is set to a value equal to or more than the lower limit of the above range, the thermal decomposition of fluoromethanes is promoted, and R-1132(E) is obtained efficiently. When the residence time is set to a value equal to or less than the upper limit of the above range, fluoromethanes and R-1132(E) are less likely to undergo caulking, thus improving the productivity. When the reaction temperature is set to 850° C. or higher for the purpose of simultaneously producing R-1132(E) and R-1123, it is preferable to set the residence time to 0.1 to 0.5 seconds.

The reaction gas containing R-1132(E) obtained in embodiment 2 may be appropriately subjected to a purification step to extract high-purity R-1132(E). The purification method may be a known purification method, such as distillation.

Embodiment 3

Embodiment 3 relates to a method for producing a reaction gas containing R-1132(E), (1) the method comprising a step of subjecting a starting material gas containing one or more fluoromethanes selected from the group consisting of chlorodifluoromethane (R-22), chlorofluoromethane (R-31), difluoromethane (R-32), and fluoromethane (R-41) to a reaction that involves thermal decomposition to obtain the reaction gas, and (2) the starting material gas containing one or more inert gases selected from the group consisting of nitrogen, argon, hydrofluorocarbons, and carbon dioxide in the content of 10 to 90 volume %.

The starting material gas contains one or more fluoromethanes selected from the group consisting of chlorodifluoromethane (R-22), chlorofluoromethane (R-31), difluoromethane (R-32), and fluoromethane (R-41), which are capable of synthesizing a reaction gas containing R-1132(E), which is the target compound, by a reaction that involves thermal decomposition. Among these fluoromethanes, R-32 is preferable to achieve easy separation of by-products, reduction of the number of steps such as rectification, and suppression of the formation of by-products.

In embodiment 3, the starting material gas contains one or more inert gases selected from the group consisting of nitrogen, argon, hydrofluorocarbons, and carbon dioxide in the content of 10 to 90 volume %. That is, in embodiment 3, the fluoromethanes (one or more members selected from the group consisting of R-22, R-31, R-32, and R-41) are diluted for use with the inert gas used as a diluent gas. Examples of the hydrofluorocarbons include one or more members selected from the group consisting of 1,1,2,2- tetrafluoroethane (R134), 1,1,1,2-tetrafluoroethane (R134a), and pentafluoroethane (R125).

In embodiment 3, the starting material gas contains the inert gas in the content of 10 to 90 volume %. Due to this, both the conversion of fluoromethanes and the selectivity of R-1132(E) can be improved more than in known methods. In particular, the selectivity of R-1132(E) in the reaction gas can be increased to 15 mol % or more, which is a great advantage over known techniques.

In embodiment 3, the starting material gas contains the inert gas in the content of preferably 30 to 90 volume %, more preferably 50 to 89 volume %, and particularly preferably 70 to 88 volume %.

In embodiment 3, it is also possible to supply the starting material gas after the starting material gas is preheated to an arbitrary temperature, if necessary.

The temperature (reaction temperature) at which the starting material gas is subjected to the reaction is preferably 750 to 1050° C., more preferably 800 to 950° C., and still more preferably 850 to 900° C. When the reaction temperature is set within this range, both the conversion of fluoromethanes and the selectivity of R-1132(E) can be improved. In particular, when the reaction temperature is set to 850° C. or higher, trifluoroethylene (R-1123) is easily contained in the reaction gas in addition to R-1132(E). This is advantageous because R-1132(E) and R-1123, which are promising refrigerants, can be simultaneously produced. To achieve such simultaneous production, the reaction temperature is preferably set to 850 to 1050° C., more preferably 850 to 950° C., and particularly preferably 850 to 900° C.

The heating method used when subjecting the starting material gas to the reaction may be a known method. Examples include a method of heating a reactor (reaction container) in an electric furnace, a method of heating a reactor with an electric heater or a jacket through which a heat medium is circulated, a method of heating a reactor in a microwave oven, and a method in which the inert gas as a diluent gas is heated and then mixed with fluoromethanes.

The pressure (reaction pressure) at which the starting material gas is supplied to the reaction is preferably 0 to 0.6 MPaG, and more preferably 0 to 0.3 MPaG. By setting the pressure within this range, both the conversion of fluoromethanes and the selectivity of R-1132(E) can be improved. The lower limit of the pressure can be set to, for example, 0.01 MPaG or 0.1 MPaG.

The time (residence time) for subjecting the starting material gas to the reaction is in accordance with the type of fluoromethanes, reaction temperature, reaction pressure, and the like; and cannot be unconditionally determined. However, it is preferably 0.2 to 3 seconds, and more preferably 0.5 to 1 second. When the residence time is set to a value equal to or more than the lower limit of the above range, the thermal decomposition of fluoromethanes is promoted, and R-1132(E) is obtained efficiently. When the residence time is set to a value equal to or less than the upper limit of the above range, side reactions are suppressed, and thermal decomposition of fluoromethanes is promoted, improving the productivity. When the reaction temperature is set to 850 to 1050° C. for the purpose of simultaneously producing R-1132(E) and R-1123, it is preferable to set the residence time to 0.1 to 0.5 seconds.

The form of the reactor in which the starting material gas is subjected to the reaction is not limited, and known reactors capable of withstanding the reaction temperature and reaction pressure stated above are widely usable. For example, a tubular flow reactor packed with a catalyst may be used. Examples of the catalyst include metal oxide catalysts, such as $Al_2O_3$ and $CoO_2$; metal catalysts, such as Fe, Zn, and Co; and catalysts in which metal particles are supported on oxide or carbon carriers, such as Pd/C and $Pd/TiO_2$. When the reaction is performed in the absence of a catalyst, the reactor may be, for example, a hollow adiabatic reactor, or an adiabatic reactor packed with a porous or non-porous metal or medium that improves the mixing state of the starting material gas. Also usable is a multitubular reactor or the like in which a heat medium is used to cool the reactor and/or to homogenize the temperature distribution within the reactor.

When a hollow reactor is used, in a method wherein a reactor with a smaller inner diameter is used to improve heat transfer efficiency, it is preferable, for example, that the relationship between the flow rate of the starting material gas and the inner diameter of the reactor be adjusted so that a high linear velocity and a large heat transfer area are obtained.

Specifically, the reactor is preferably formed of a material that is resistant to the corrosive action, such as Hastelloy, Inconel, Monel, Incoloy, and stainless steel materials (e.g., SUS316). As described above, when a metal reactor with an iron content of 10 mass % or less, such as a reactor of Hastelloy or Inconel, is used from among the reactors above, the occurrence of caulking on the reactor inner wall can also be suppressed in a manner more excellent than in known methods.

The reaction gas containing R-1132(E) obtained in embodiment 3 may be appropriately subjected to a purification step to extract high-purity R-1132(E). The purification method may be a known purification method, such as distillation.

Embodiment 4

Embodiment 4 relates to a method for producing a reaction gas containing R-1132(E),
(1) the method comprising a step of subjecting a starting material gas containing one or more fluoromethanes selected from the group consisting of chlorodifluoromethane (R-22), chlorofluoromethane (R-31), difluoromethane (R-32), and fluoromethane (R-41) to a reaction that involves thermal decomposition to obtain the reaction gas, and
(2) the starting material gas containing the fluoromethanes in the content of 90 to 100 volume %.

The starting material gas contains one or more fluoromethanes selected from the group consisting of chlorodifluoromethane (R-22), chlorofluoromethane (R-31), difluoromethane (R-32), and fluoromethane (R-41), which are capable of synthesizing a reaction gas containing R-1132(E), which is the target compound, by a reaction that involves thermal decomposition. Among these fluoromethanes, R-32 is particularly preferable to achieve easy separation of by-products, reduction of the number of steps such as rectification, and suppression of the formation of by-products.

In embodiment 4, the starting material gas contains fluoromethanes (one or more members selected from the group consisting of R-22, R-31, R-32, and R-41) in the content of 90 to 100 volume %. The starting material gas contains the fluoromethanes in the content of preferably 95 to 100 volume %, more preferably 99 to 100 volume %, still more preferably 99.5 to 100 volume %, and particularly preferably 99.9 to 100 volume %. If the content of the fluoromethanes in the starting material gas is within this range, the conversion of the fluoromethanes and the selectivity of R-1132(E) can be improved, while the selectivity of carbon in the reaction gas can be reduced.

In embodiment 4, it is particularly preferable that the starting material gas has an R-32 content of 100 volume %. This can improve both the conversion of R-32 and the selectivity of R-1132(E) over known methods, and reduce the selectivity of carbon in the reaction gas.

In embodiment 4, the starting material gas preferably contains one or more inert gases selected from the group consisting of nitrogen, argon, hydrofluorocarbons, and carbon dioxide in the content of less than 10 volume %. That is, in embodiment 4, fluoromethanes are preferably diluted for use with the inert gas used as a diluent gas. Examples of the hydrofluorocarbons include one or more members selected from the group consisting of 1,1,2,2-tetrafluoroethane (R134), 1,1,1,2-tetrafluoroethane (R134a), and pentafluoroethane (R125).

In embodiment 4, the starting material gas preferably contains the inert gas in the content of less than 10 volume %. This can improve the conversion of fluoromethanes and the selectivity of R-1132(E), and reduce the selectivity of carbon in the reaction gas.

In embodiment 4, the starting material gas contains the inert gas more preferably in the content of 5 volume % or less, even more preferably 1 volume % or less, still more preferably 0.5 volume % or less, and particularly preferably 0.1 volume % or less. When the starting material gas contains the inert gas in the content within this range, the conversion of fluoromethanes and the selectivity of R-1132 (E) can be further improved, while the selectivity of carbon in the reaction gas can be further reduced. Furthermore, when the starting material gas contains the inert gas in the content within this range, R-1132(E) and the inert gas can be easily separated after the reaction that involves thermal decomposition, making it possible to reduce the production costs in terms of equipment. In embodiment 4, the content of the inert gas in the starting material gas is most preferably 0 volume %.

In embodiment 4, it is also possible to supply the starting material gas after the starting material gas is preheated to an arbitrary temperature, if necessary.

The temperature (reaction temperature) at which the starting material gas is subjected to the reaction is preferably 750 to 1050° C., and more preferably 800 to 900° C. When the reaction temperature is set within this range, both the conversion of fluoromethanes and the selectivity of R-1132 (E) can be improved. In particular, when the reaction temperature is set to 800° C. or higher, trifluoroethylene (R-1123) is easily contained in the reaction gas in addition to R-1132(E). This is advantageous because R-1132(E) and R-1123, which are promising refrigerants, can be simultaneously produced. To achieve such simultaneous production, the reaction temperature is preferably set to 800 to 900° C.

The heating method used when subjecting the starting material gas to the reaction may be a known method. Examples include a method of heating a reactor (reaction container) in an electric furnace, a method of heating a reactor with an electric heater or a jacket through which a heat medium is circulated, a method of heating a reactor in a microwave oven, and a method in which the inert gas as a diluent gas is heated and then mixed with fluoromethanes.

The pressure (reaction pressure) at which the starting material gas is supplied to the reaction is preferably 0 to 0.6 MPaG, and more preferably 0 to 0.3 MPaG. By setting the pressure within this range, both the conversion of fluoromethanes and the selectivity of R-1132(E) can be improved. The lower limit of the pressure can be set to, for example, 0.01 MPaG or 0.1 MPaG.

The time (residence time) for subjecting the starting material gas to the reaction is in accordance with the type of fluoromethanes, reaction temperature, reaction pressure, and the like; and cannot be unconditionally determined. However, it is preferably 0.03 to 5 seconds, and more preferably 0.04 to 4 seconds. When the residence time is set to a value equal to or more than the lower limit of the above range, the thermal decomposition of fluoromethanes is promoted, and R-1132(E) is obtained efficiently. When the residence time is set to a value equal to or less than the upper limit of the above range, side reactions are suppressed, and thermal decomposition of fluoromethanes is promoted, improving the productivity. When the reaction temperature is set to 750 to 1050° C. for the purpose of simultaneously producing R-1132(E) and R-1123, it is preferable to set the residence time to 0.04 to 4 seconds.

The form of the reactor in which the starting material gas is subjected to the reaction is not limited, and known reactors capable of withstanding the reaction temperature and reaction pressure stated above are widely usable. For example, a tubular flow reactor packed with a catalyst may be used. Examples of the catalyst. include metal oxide catalysts, such as $Al_2O_3$ and $CoO_2$; metal catalysts, such as Fe, Zn, and Co; and catalysts in which metal particles are supported on oxide or carbon carriers, such as Pd/C and $Pd/TiO_2$. When the reaction is performed in the absence of a catalyst, the reactor may be, for example, a hollow adiabatic reactor, or an adiabatic reactor packed with a porous or non-porous metal or medium that improves the mixing state of the starting material gas. Also usable is a multitubular reactor or the like in which a heat medium is used to cool the reactor and/or to homogenize the temperature distribution within the reactor.

When a hollow reactor is used, in a method wherein a reactor with a smaller inner diameter is used to improve heat transfer efficiency, it is preferable, for example, that the relationship between the flow rate of the starting material gas and the inner diameter of the reactor be adjusted so that a high linear velocity and a large heat transfer area are obtained.

Specifically, the reactor is preferably formed of a material that is resistant to the corrosive action, such as Hastelloy, Inconel, Monel, Incoloy, and stainless steel materials (e.g., SUS316). As described above, when a metal reactor with an iron content of 10 mass % or less, such as a reactor of Hastelloy or Inconel, is used from among the reactors above, the occurrence of caulking on the reactor inner wall can also be suppressed in a manner more excellent than in known methods. In embodiment 4, it is particularly preferable to use a reactor of Inconel as the metal reactor with an iron content of 10 mass % or less The reaction gas containing R-1132(E) obtained in embodiment 4 may be appropriately subjected to a purification step to extract high-purity R-1132(E). The purification method may be a known purification method, such as distillation.

2. Composition

The composition according to the present disclosure comprises (E)-1,2-difluoroethylene (R-1132(E)) and one or more compounds selected from the group consisting of 3,3,3-trifluoropropyne (TFP), propyne, and 1,1,1,2-tetrafluoroethane (R-134a).

The composition according to the present disclosure preferably comprises R-1132(E) obtained by the production methods described in embodiments 1 to 4 above, and one or more compounds selected from the group consisting of TFP, propyne, and R-134a.

The composition according to the present disclosure more preferably comprises R-1132(E) obtained by the production methods described in embodiments 1 to 4 above, and one or more compounds selected from the group consisting of TFP and R-134a.

The composition according to the present disclosure particularly preferably comprises R-1132(E) obtained by the production methods described in embodiments 1 to 4 above, TFP, and R-134a.

In the composition of present disclosure, it is preferable that the TFP content is 1 mass % or less based on the total content of the composition.

In the composition of present disclosure, the TFP content is more preferably 0.3 mass % or less based on the total content of the composition, and the R-134a content is more preferably 0.2 mass % or less based on the total content of the composition.

The embodiments of the present disclosure are described as above. However, the present disclosure is not limited to these embodiments, and can include various embodiments as long as they do not deviate from the gist of the disclosure.

EXAMPLES

The production methods according to embodiments 1 to 4 of the present disclosure are described in more detail below with reference to Examples. However, the production methods of the present disclosure are not limited to the scope of the Examples.

In Examples 1-9 below, the composition of each component was analyzed by gas chromatography (MS detector).

Examples 1 to 3

Embodiment 1

Effect of Water Vapor Content on Reaction Results

Under the reaction conditions shown in Table 1, a reaction gas containing R-1132(E) was obtained by subjecting a starting material gas containing only R-32 as fluoromethanes to a reaction that involves thermal decomposition. The reaction results of Example 2 show a higher yield of R-1132(E) than those shown in the reaction results of Examples 1 and 3.

TABLE 1

|  | Ex. 1 | Ex. 2 | Ex. 3 |
|---|---|---|---|
| Reaction conditions | | | |
| Material of reaction tube | SUS316 | SUS316 | SUS316 |
| Temperature (° C.) | 850 | 850 | 850 |
| Pressure (MPaG) | 0.01 | 0.01 | 0.01 |
| Residence time (sec) | 0.3 | 0.3 | 0.3 |
| Composition of diluent gas | | | |
| Water vapor content in starting material gas (volume %) | 90 | 0.1 | 2 |
| Nitrogen content in starting material gas (volume %) | 0 | 89.9 | 88 |

TABLE 1-continued

|  | Ex. 1 | Ex. 2 | Ex. 3 |
|---|---|---|---|
| Reaction results | | | |
| Conversion of starting material gas | 20.0% | 6.10% | 6.80% |
| Yield of R-1132(E) | 0.24% | 0.93% | 0.92% |
| Selectivity in reaction gas | | | |
| $CH_4$ | 9.7% | 5.8% | 7.0% |
| $CO_2$ | 7.4% | 3.5% | 6.3% |
| R23 | 2.1% | 0.0% | 0.0% |
| $CH_2=CH_2$ | 1.5% | 0.0% | 1.2% |
| $CF_2=CH_2$ | 7.5% | 5.8% | 7.5% |
| $CH\equiv CH$ | 2.3% | 0.0% | 0.0% |
| $CF_2=CHF$ (R-1123) | 1.2% | 4.7% | 9.1% |
| $CH_2=CHF$ | 5.5% | 0.0% | 0.0% |
| R41 | 9.3% | 12.9% | 11.3% |
| R-1132(E) | 1.2% | 15.3% | 13.5% |
| R125 | 0.2% | 0.0% | 0.0% |
| 143a | 0.5% | 0.0% | 0.0% |
| Propyne | 0.1% | 0.0% | 0.0% |
| TFP | 0.2% | 0.0% | 0.0% |
| R-1132(Z) | 1.8% | 24.7% | 22.3% |
| $CF_3CHCHF$ | 0.1% | 0.0% | 0.0% |
| R-134a | 7.1% | 0.0% | 0.0% |
| FC-4223ZC | 0.6% | 0.0% | 0.0% |
| R134 | 18.7% | 5.8% | 15.8% |
| R143 | 1.6% | 21.5% | 6.0% |
| Others H.B. | 21.4% | 0.0% | 6% |

Examples 4 and 5

Embodiment 2

Effect of Reactor Material on Reaction Results

Under the reaction conditions shown in Table 2, a reaction gas containing R-1132(E) was obtained by subjecting a starting material gas containing only R-32 as fluoromethanes to a reaction that involves thermal decomposition. The reaction results of Example 4 show both higher conversion of R-32 and higher yield of R-1132(E), compared to the reaction results of Example 5. The reaction results of Example 4 also show that $CO_2$ was not generated, and that a smaller content of carbon was attached to the reactor inner wall (caulking was suppressed), compared to the reaction results of Example 5.

TABLE 2

|  | Ex. 4 | Ex. 5 |
|---|---|---|
| Reaction conditions | | |
| Type of diluent gas | N2 | N2 |
| Material of reaction tube | INCONEL 600 | SUS316 |
| Reaction temperature (° C.) | 850 | 850 |
| Residence time (sec) | 0.30 | 0.30 |
| Diluent gas content in starting material gas (volume %) | 90 | 90 |
| Reaction duration (hr) | 36 | 36 |
| Reaction results | | |
| Conversion of starting material gas | 7.30% | 6.10% |
| Yield of R-1132(E) | 1.20% | 0.93% |
| Selectivity in reaction gas | | |
| $CH_4$ | 1.2% | 5.8% |
| $CO_2$ | 0.0% | 3.5% |
| R23 | 1.6% | 0.0% |
| $CF_2=CH_2$ | 7.1% | 5.8% |
| $CF_2=CHF$(R-1123) | 12.9% | 4.7% |
| $CH_2=CHF$ | 1.2% | 0.0% |

TABLE 2-continued

|  | Ex. 4 | Ex. 5 |
| --- | --- | --- |
| R41 | 6.7% | 12.9% |
| R-1132(E) | 16.5% | 15.3% |
| R-1132(Z) | 23% | 24.7% |
| R134 | 22% | 5.8% |
| R143 | 7.5% | 21.5% |
| Content of carbon attached to reactor tube wall (mg) | 13 | 44 |

Examples 6 and 7

Embodiment 3

Effect of Difference between R-32 and R-31 Using 90 Volume % of Inert Gas on Reaction Results Under the reaction conditions shown in Table 3, a reaction gas containing R-1132(E) was obtained by subjecting a starting material gas containing fluoromethanes (R-32 or R-31) to a reaction that involves thermal decomposition. Under the same conditions (i.e., the content of the inert gas (diluent gas) contained in the starting material gas was set to 90 volume %), the reaction results of Example 6, in which a starting material gas that contained only R-32 as fluoromethanes was used, show a higher yield of R-1132(E) compared to the reaction results of Example 7, in which a starting material gas that contained only R-31 as fluoromethanes was used. These results indicate that R-32 is more preferable than R-31 as the fluoromethanes contained in the starting material gas.

Examples 6, 8, and 9

Embodiment 3

Effect of Difference in Reaction Temperature Using 90 Volume % of Inert Gas on Reaction Results Under the reaction conditions shown in Table 4, a reaction gas containing R-1132(E) was obtained by subjecting a starting material gas containing only R-32 as fluoromethanes to a reaction that involves thermal decomposition. Comparison was made under the same conditions except that the reaction temperature was 850° C. in Example 6, and the reaction temperatures were 950° C. and 1050° C. in Example 8 and Example 9, respectively. The results reveal that as the reaction temperature increased, the conversion of R-32 and the yield of R-1132(E) were both increased. The results also reveal that as the reaction temperature increased, the percentages of the production amounts of R-1132(E) and trifluoroethylene (R-1123) both increased. These results indicate that it is advantageous to set the reaction temperature higher for the purpose of simultaneous production.

TABLE 4

|  | Ex. 6 | Ex. 8 | Ex. 9 |
| --- | --- | --- | --- |
| Reaction conditions | | | |
| Type of diluent gas | $N_2$ | $N_2$ | $N_2$ |
| Material of reaction tube | SUS316 | SUS316 | SUS316 |
| Temperature (° C.) | 850 | 950 | 1050 |
| Pressure (MPaG) | 001 | 0.01 | 0.01 |

TABLE 3

|  | Ex. 6 |  | Ex. 7 |
| --- | --- | --- | --- |
| Reaction conditions |  | Reaction conditions |  |
| Type of diluent gas | $N_2$ | Type of diluent gas | $N_2$ |
| Starting material gas | R32 | Starting material gas | R31 |
| Material of reaction tube | SUS316 | Material of reaction tube | SUS316 |
| Reaction temperature (° C.) | 850 | Reaction temperature (° C.) | 850 |
| Residence time (sec) | 0.3 | Residence time (sec) | 0.3 |
| Diluent gas content in starting material gas (volume %) | 90 | Diluent gas content in starting material gas (volume %) | 90 |
| Reaction results |  | Reaction results |  |
| Conversion of starting material gas | 6.10% | Conversion of starting material gas | 16.30% |
| Yield of R-1132(E) | 0.93% | Yield of R-1132(E) | 0.72% |
| Selectivity in reaction gas |  | Selectivity in reaction gas |  |
| CH4 | 5.8% | CH2=CHF | 3.5% |
| CO2 | 3.5% | R-1132(Z) | 9.0% |
| R23 | 0.0% | R-1132(E) | 4.4% |
| CF2=CH2 | 5.8% | R40 | 4.8% |
| CF2=CHF (R-1123) | 4.7% | R41 | 14.3% |
| CH2=CHF | 0.0% | R23 | 2.1% |
| R41 | 12.9% | R32 | 1.2% |
| R-1132(E) | 15.3% | CF2=CH2 | 2.5% |
| R-1132(Z) | 24.7% | CF2=CHF (R-1123) | 5.9% |
| R134 | 5.8% | TFP | 0.9% |
| R143 | 21.5% | CClF=CH2 | 1.2% |
|  |  | CF2=CHCl | 1.0% |
|  |  | CFCl=CHF | 173% |
|  |  | CHCl=CHF | 8.2% |
|  |  | Butadiene | 0.2% |
|  |  | CH2Cl2 | 3.6% |
|  |  | CClF=CHCl | 4.9% |
|  |  | HB | 14.9% |

TABLE 4-continued

|  | Ex. 6 | Ex. 8 | Ex. 9 |
|---|---|---|---|
| Residence time (sec) | 0.3 | 0.29 | 0.29 |
| Diluent gas content in starting material gas (volume %) | 90 | 90 | 90 |
| Reaction results | | | |
| Conversion of starting material gas | 6.10% | 8.06% | 22.30% |
| Yield of R-1132(E) | 0.93% | 1.36% | 2.23% |
| Selectivity in reaction gas | | | |
| CH4 | 5.8% | 3.6% | 4.5% |
| CH≡CH | 0.0% | 0.0% | 13.7% |
| CO2 | 3.5% | 6.1% | 12.9% |
| R23 | 0.0% | 0.0% | 0.0% |
| CF2=CH2 | 5.8% | 7.0% | 11.7% |
| CF2=CHF(R-1123) | 4.7% | 9.7% | 13.6% |
| R41 | 12.9% | 13.9% | 11.8% |
| R-1132(E) | 15.3% | 16.9% | 10.0% |
| R-1132(Z) | 24.7% | 23.3% | 13.1% |
| R134 | 5.8% | 15.5% | 4.1% |
| R143 | 21.5% | 4.0% | 0.0% |
| HB | 0.0% | 0.0% | 5% |

In Examples 10 to 17 below, the composition of each component was analyzed by gas chromatography (FID detector).

Examples 10 to 17

Embodiment 4

Effect of Content of Fluoromethanes Contained in Starting Material Gas on Reaction Results Under the reaction conditions shown in Table 5, a reaction gas containing R-1132(E) was obtained by subjecting a starting material gas containing only R-32 as fluoromethanes to a reaction that involves thermal decomposition. The "Others" in Table 5 represent, for example, fluorocarbons with 3 to 6 carbon atoms, and the like. Examples of the fluorocarbons with 3 to 6 carbon atoms include 1,1,2-trifluoro-1,3-butadiene and 1,3,5-trifluorobenzene.

The reaction results of Examples 12 to 17 show a higher yield of R-1132(E) than that of the reaction results of Example 11. The reaction results of Examples 13 and 17, as well as the results of Example 10, show a comparable yield of R-1132(E); however, the reaction results of Examples 13 and 17 show a significantly reduced selectivity of carbon (C) in the reaction gas as compared to the results of Example 10. These results reveal that, to achieve effects, i.e., to reduce the selectivity of carbon in the reaction gas and to improve the yield of R-1132(E), it was particularly advantageous not to dilute the starting material gas with nitrogen (nitrogen content in the starting material gas=0 volume %). Considering the cost for separating the diluent gas in a subsequent step, these results confirmed that it is advantageous to set the R-32 content in the starting material gas to 90 to 100 volume %, and that it is particularly advantageous to set the R-32 content in the starting material gas to 100 volume %.

TABLE 5

| | | Ex. 10 | Ex. 11 | Ex 12 | Ex. 13 | Ex 14 | Ex. 15 | Ex 16 | Ex. 17 |
|---|---|---|---|---|---|---|---|---|---|
| Reaction conditions | Starting material gas | R-32 | R-32 | R-32 | R-32 | R-32 | R-32 | R-32 | R-32 |
| | Flow rate of starting material gas (mL/min) | 35.0 | 369.4 | 177.0 | 368.0 | 119.4 | 129.8 | 264.3 | 172.9 |
| | Type of diluent gas | $N_2$ | $N_2$ | — | — | — | — | — | — |
| | Flow rate of diluent gas (mL/min) | 300.9 | 393 | 0 | 0 | 0 | 0 | 0 | 0 |
| | Material of reaction tube | INCONEL 600 | INCONEL 600 | INCONEL 600 | INCONEL 600 | INCONEL 600 | INCONEL 600 | INCONEL 600 | INCONEL 600 |
| | Reaction temperature (° C.) | 950 | 900 | 900 | 900 | 900 | 800 | 800 | 800 |
| | Residence time (sec) | 0.200 | 0.160 | 0.180 | 0.560 | 0.370 | 11.380 | 5.590 | 8.540 |
| | R-32 content in starting material gas (volume %) | 10 | 90 | 100 | 100 | 100 | 100 | 100 | 100 |
| | Diluent gas content in starting material gas (volume %) | 90 | 10 | 0 | 0 | 0 | 0 | 0 | 0 |
| | Water vapor content in starting material gas (volume %) | 0 | 0 | 0 | 0 | 0 | 0 | 0 | 0 |
| Reaction results | Conversion of starting material gas | 5.8% | 1.5% | 4.1% | 1.6% | 5.6% | 5.4% | 3.1% | 4.8% |
| | Yield of R-1132(E) | 1.2% | 0.6% | 1.2% | 0.7% | 1.5% | 1.2% | 1.0% | 1.2% |

TABLE 5-continued

|  |  | Ex. 10 | Ex. 11 | Ex 12 | Ex. 13 | Ex 14 | Ex. 15 | Ex 16 | Ex. 17 |
|---|---|---|---|---|---|---|---|---|---|
| Selectivity in reaction gas | CH4 | 0.3% | 0.2% | 0.2% | 0.1% | 0.3% | 0.4% | 0.2% | 0.3% |
| | R23 | 0.4% | 0.4% | 0.7% | 0.4% | 1.0% | 1.8% | 1.1% | 1.8% |
| | 2F (R1132a) | 32% | 3.2% | 3.2% | 3.2% | 3.1% | 2.2% | 2.4% | 2.3% |
| | C2H2 | 1.1% | 0.9% | 1.5% | 1.0% | 1.6% | 1.3% | 1.3% | 1.4% |
| | 3FH (R-1123) | 5.7% | 4.7% | 4.1% | 4.5% | 3.8% | 1.2% | 1.8% | 1.4% |
| | R41 | 4.9% | 10.1% | 9.4% | 10.0% | 8.8% | 8.2% | 9.8% | 8.6% |
| | R-1132(E) | 8.0% | 10.0% | 8.2% | 9.7% | 7.2% | 4.5% | 6.5% | 5.0% |
| | R143a | 0.0% | 0.2% | 0.3% | 0.3% | 0.4% | 0.6% | 0.5% | 0.5% |
| | R-1132(Z) | 11.6% | 15.4% | 12.6% | 15.0% | 11.1% | 7.4% | 10.4% | 8.1% |
| | R134a | 0.3% | 2.4% | 3.3% | 2.6% | 3.8% | 5.2% | 4.2% | 4.8% |
| | R134 | 8.8% | 17.2% | 17.0% | 17.5% | 16.6% | 16.7% | 18.2% | 16.9% |
| | R152a | 0.1% | 0.1% | 0.0% | 0.1% | 0.0% | 0.0% | 0.1% | 0.1% |
| | R143 | 4.0% | 15.7% | 12.0% | 162.% | 9.9% | 11.1% | 16.4% | 12.0% |
| | Others | 6.8% | 9.4% | 17.1% | 10.4% | 20.3% | 24.4% | 15.5% | 23.9% |
| | C | 44.9% | 10.2% | 10.3% | 8.9% | 12.3% | 14.8% | 11.8% | 12.9% |

Example 18

Confirmation of Characteristics as a Refrigerant

The global warming potential (GWP) of the mixed refrigerant of Example 18 and that of Reference Example 1 (R410A) was evaluated based on the values in the Fourth Assessment Report of the Intergovernmental Panel on Climate Change (IPCC).

The coefficient of performance (COP) of these mixed refrigerants was determined by performing theoretical refrigeration cycle calculations for mixed refrigerants using Refprop 10.0 (the National Institute of Science and Technology (NIST)) under the following conditions.

Evaporating temperature: 10° C.

Condensation temperature: 45° C.

Superheating temperature: 5 K

Subcooling temperature: 5 K

Compressor efficiency: 70%

The coefficient of performance (COP) was determined by the following formula.

$$COP = (\text{refrigerating capacity or heating capacity}) / \text{power consumption}$$

TABLE 6

|  | Ref. Ex. 1<br>R410A<br>(R32 = 50 mass %,<br>R125 = 50 mass %) | Ex. 18<br>R-1132(E) = 99.5 mass %,<br>R-134a = 0.2 mass %,<br>TFP = 0.3 mass % |
|---|---|---|
| COP | 4.49 | 4.50 |
| GWP | 2090 | 4 |

The results confirmed that the mixed refrigerant of Example 18 had characteristics of a COP equivalent to that of R410A, and a sufficiently low GWP.

The invention claimed is:

1. A method for producing a reaction gas containing (E)-1,2-difluoroethylene (R-1132(E)),
   (1) the method comprising a step of subjecting a starting material gas containing 99 to 100 volume % of difluoromethane (R-32) to a reaction that involves thermal decomposition to obtain the reaction gas, and
   (2) the reaction being performed at a temperature of 750 to 1050° C.

2. The production method according to claim 1, wherein the reaction is performed at a pressure of 0 to 0.6 MPaG.

3. The production method according to claim 1, wherein the reaction is performed for a residence time of 0.03 to 11.380 seconds.

* * * * *